United States Patent [19]

Greco et al.

[11] 4,333,881

[45] Jun. 8, 1982

[54] PROCESS FOR REDUCING METAL ALKOXIDES, AND THE USE OF THE COMPOUNDS SO OBTAINED

[75] Inventors: Alberto Greco, Dresano; Guglielmo Bertolini, Pavia, both of Italy

[73] Assignees: Anic S.p.A., Palermo; Snamprogetti S.p.A., Milan, both of Italy

[21] Appl. No.: 124,148

[22] Filed: Feb. 25, 1980

[30] Foreign Application Priority Data

Mar. 7, 1979 [IT] Italy .............................. 20798 A/79

[51] Int. Cl.$^3$ ........................... C07F 9/00; C07F 7/28; C07F 7/00; C07F 11/00
[52] U.S. Cl. .............................. 260/429 R; 260/429.3; 260/429.5; 260/438.5 R
[58] Field of Search ......... 260/429.5, 429 R, 438.5 R, 260/429.3

[56] References Cited

U.S. PATENT DOCUMENTS 3,906,017  9/1975  Middleton et al. ...... 260/429 AR X

OTHER PUBLICATIONS

Bradley et al., Metal Alkoxides, Academic Press, N.Y., pp. 37–41 (1978).

*Primary Examiner*—Helen M. S. Sneed
*Attorney, Agent, or Firm*—Morgan, Finnegan, Pine, Foley & Lee

[57] ABSTRACT

Alkoxides of transition metals, selected from among tetravalent Ti, tetravalent and pentavalent V, tetravalent Cr and tetravalent Zr, actinides and lanthanides, are reduced to corresponding alkoxides of lower valency by reacting such higher valency metal alkoxides, in liquid phase, with vapors of metals of the alkaline earth group, the III group and the IV group metals and magnesium. Very efficient polymerization catalysts for the polymerization of unsaturated compounds are thus obtained.

4 Claims, No Drawings

PROCESS FOR REDUCING METAL ALKOXIDES, AND THE USE OF THE COMPOUNDS SO OBTAINED

This invention relates to a process for reducing alkoxides of metals chosen from Ti (4+), V (4+), V (5+), Cr (4+), Zr (4+), and elements belonging to the lanthanide and actinide series.

Said process consists of reducing the aforesaid alkoxides with the vapour of metals chosen from the alkaline earth metals, metals pertaining to groups III and IV, or manganese. (The use of a solvent medium for the alkoxides is not indispensable). The applicant is familiar with the existence of U.S. Patent Application Ser. No. 763.077 filed on Jan. 27, 1977 relating to a method for preparing titanium and vanadium trichlorides starting from their respective tetrachlorides by reduction by the vapour of metals chosen from Al, Mg, Cr, Mn, Fe, V and Ti.

The use of reduction by metal vapour in the case of the aforesaid alkoxides cannot be considered to be an expected or foreseeable result on the basis of the above mentioned patent application, as the stability of the bonds involved in the reduction is quite different in the two cases.

In this respect, in the case of the titanium chloride, the reduction involves the breaking of metal-chlorine bonds, and the driving force of the reaction can be the force of formation of insoluble ionic $TiCl_3$, whereas in the present case the bond concerned is the metal-oxygen bond, which is more covalent than the Me-Cl bond, and the products are not of saline character.

In the case of alkoxides, it was therefore impossible to forecast that certain metals in their vapour state would be able to quantitatively break a large range of transition metal-oxygen bonds such as defined herein, under very mild reaction conditions such as those claimed for the reduction of the chlorides.

As a demonstration of this, it should be noted that according to the previous patent application, while it is practically possible to break transition metal-chlorine bonds by all metals in the form of vapour, only the metals chosen from the alkaline earth metals, groups III and IV or manganese can break metal-alkoxide bonds.

In contrast to the previous patent application, the stability of the metal-oxygen bond excludes the possibility of using, inter alia, zinc, antimony, tellurium and iron, which are used in the reduction of $TiCl_4$.

It should also be noted that the processes for preparing titanium (3+) alkoxides already known from the literature differ substantially from the process discovered by us.

In this respect, we can cite the preparation of Ti $(OR)_3$ starting from $TiCl_3$ and alcoholates of alkaline metals (A. W. Adams et Al. Austral. J. Chem. 19 (1966) 207), or starting from Ti (III) amides by alcoholysis (Lappert and Singer, J. Chem. Soc. (1971) 1314), or by reduction of titanium tetraalkoxides to titanium trialkoxide polymers using lithium, potassium or other alkaline metals in alcohols or ethers (A. N. Nermeyanov et al. Dokl, Akad. Nank. SSSR, 95 (1954) 813).

The main limitation of the stated preparation methods is that they are limited to the use of alkaline metals in solvents containing hydroxyl or polar groups.

In contrast, the reduction of titanium tetraalkoxides to titanium trialkoxides or the reduction of alkoxides of other transition metals by our process can also take place in the absence of solvents or in solvents completely apolar such as petroleum, and leads to solutions or suspensions of titanium (3+) alkoxides mixed with alkoxides of the metal used for the reduction. If stoichiometric quantities of Ti $(OR)_4$ (or of another transition metal alkoxide) and the reducing metal are used, then the reaction can be expressed by the equation $$n\ Ti\ (OR)_4 + M\ (vap) \rightarrow Ti\ (OR)_{3n}.M\ (OR)_n$$

where n is the valency assumed by the metal used as the reducing agent. However, if the metal used as the reducing agent is evaporated in an excess of Ti $(OR)_4$, it is sometimes possible to isolate the Ti $(OR)_3$ at a good level of purity.

This is because the excess of Ti $(OR)_4$, as is the case of Ti (O n-butyl)$_4$ with respect to the stoichiometric quantity required by the quantity of metal evaporated, has no damaging effect on the nature of the product, in this case $[Ti\ (O\text{-}n\text{-}butyl)_3]_x$ which forms in the reaction, whereas it can compete with the Ti (3+) and complex the magnesium alkoxide to give mixed soluble alkoxides, which can be easily separated from the $[Ti\ (O\text{-}n\text{-}butyl)_3]_x$ polymer, which is insoluble and can therefore be separated in a good state of purity by filtration (Ex. 1, test 2 of table 1).

A different case is represented by the reduction of Ti $(O\text{—}i\text{—}C_3H_7)_4$ by Mg vapour. In this case the $[Ti\ (O\text{—}i\text{—}C_3H_7)_3]_y$ has good solubility, while the Mg $(O\text{—}i\text{—}C_3H_7)_2$ tends to precipitate, and can be separated by filtration.

In this case, if it is the $[Ti\ (O\text{—}i\text{—}C_3H_7)_3]_y$ which is of interest, then it is advisable to operate with the stoichiometric quantities required by the reaction $(Ti^{4+}/Mg=2)$.

If Mg is replaced by Al as the reducing metal, then in all cases mixed $Ti^{3+}$—Al alkoxides are obtained, even when operating with a large excess of Ti $(OR)_4$ (ex. 3). The problem of obtaining pure $Ti^{3+}$ alkoxides obviously does not exist when titanium itself is used as the reducing metal (ex. 4). The reduction of $Ti^{4+}$ (or of other transition metals) to a valency lower than 3, or to the maximum valency compatible with the transition metal alkoxide, can be easily carried out using the reduction method described herein, as demonstrated by test 6 of Ex. 1, table 1, where magnesium is used for reducing $Ti^{4+}$ to $Ti^{2+}$. In this case only the mixed alkoxide is isolated. On the basis of these considerations, even though in the process according to the invention it is preferable to carry out the reduction with the stoichiometric quantity of the transition metal alcoholate required by the metal to be evaporated, an excess of transition metal alcoholate over this quantity (10–30 times) can sometimes be necessary especially if this can enable the transition metal alcoholate in a reduced form to be isolated at a good level of purity. According to the present invention, the tetraalkoxide is reduced by the following method in the reactor described in the above mentioned patent appln. The metal is evaporated slowly (1–5 g/hr) and made to react with the titanium (4+) alkoxide (or another transition metal alkoxide) either in its pure state or dissolved, to give a 0.2–2 mol solution, in hydrocarbon, including a halogenated hydrocarbon provided the halogen reacts only slightly or not at all with the metal vapour, or in an ether or thioether. The solvents can also be cyclic. Particularly suitable for this purpose are all linear and cyclic aliphatic and aromatic hydrocarbons, including heterocyclic hydrocarbons, such as vaseline oil, kerosene, heptane, xylene, cyclohexane, decahydronaphthalene, cumene, mesitylene, ethylbenzene, toluene, pyridine and quinoline. Suitable halogenated solvents include fluorobenzene, hexachlorobutadiene. Suitable ethers include diethyl ether, isoamyl ether, butylether, anisole, dioxane, tetrahydrofuran etc. Suitable thioethers include diphenylsulphide and thioanisole. Suitable inorganic solvents include polycyclosiloxanes or silicone oils with a limited number of hydroxyls, etc.

All the alkoxides of the transition metals are suitable for reduction, provided they satisfy the condition of being in a high valency state, and have a certain solubility in at least one of the said solvents.

In the Ti $(OR)_4$ compounds, R can be an alkyl, cycloalkyl or aromatic radical (e.g. $R=CH_3$, $CH_2CH_3$, n-$C_3H_7$, i-$C_3H_7$, n-$C_4H_9$, i-$C_4H_9$, t-$C_4H_9$, 2 ethyl-hexyl etc.) or an inorganic radical such as Si $(CH_3)_4$, or contain mixed ligands of the aforesaid type.

Mixed alkoxides can also be used as the materials to be reduced, such as $M[Ti (OR)_6]$ (M=Mg, Ca), or $M'H[Ti (OR)_6]_2$ (M'=Li, Na).

The vanadium alkoxides include $V(O-t-C_4H_9)_4$ and $VO(O-i-C_3H_7)_3$. The temperature of the reaction flask is preferably kept between $-30°$ and $+20°$ C. during the reaction, but the temperature limits can be considerably wider, because the reaction takes place even when the reaction flask is cooled to the temperature of liquid nitrogen.

On completing the reaction by vaporisation, the mixture can be stirred at ambient temperature or can be heated at moderate temperature, generally less than 150° C., and normally between 60° and 130° C. This treatment is not indispensable on completing the reaction, but it favours precipitation of the mixed titanium polymer alkoxides in reduced form by accelerating it, so allowing their separation by filtration or centrifuging from the solvent and that alkoxide still present due to deficiency of the reducing metal.

In the case of reduction of $Ti^{4+}$ alkoxides, the material from the reaction flask is in the form of a homogeneous solution from which the $Ti^{3+}$ or mixed alkoxides separate only very slowly if the heat treatment is not given.

The mixed alkoxides can be obtained by removing the reaction solvent by distillation or under vacuum, especially when stoichiometric quantities of reducing metal, Ti $(OR)_4$ or other transition metal alkoxides are used.

The $Ti^{3+}$ alkoxides or mixed alkoxides—even of other transition metals—are in the form of largely amorphous green coloured powders which are weakly paramagnetic.

They are not further soluble after precipitation from their mother solutions, and it can therefore be considered that their polymerisation process is a typically irreversible fact. All the materials are sensitive to atmospheric oxygen and humidity. When reduction is proceeded as far as $Ti^{2+}$, the material is pyrophoric, and must be handled with extreme care.

The $Ti^{3+}$ alkoxides or mixed $Ti^{3+}$ alkoxides prepared by us find useful application in the preparation of catalytic systems for the polymerisation and copolymerisation of a large series of unsaturated substrates if they are subjected to preliminary treatment with chlorinating agents chosen from $BCl_3$, $BBr_3$, $SiCl_4$, $SiBr_4$, $TiCl_4$, $TiBr_4$, $TiI_4$, $Ti(OR)_2Cl_2$, $GeCl_4$, $SnCl_4$, $SbCl_5$, $POCl_3$, $PCl_5$, $SOCl_2$, $MoCl_5$, $CrO_2Cl_2$, $MoOCl_4$, $WOCl_4$, $VCl_4$ and $VOCl_3$. They are then reacted with organometallic compounds of the group III metals for the polymerisation and copolymerisation of a large number of organic substrates containing at least one vinyl, norbornenyl or cyclohexyl group.

The halogenation can be carried out either directly on the mother solutions from the reactor where reduction has taken place by metal vapour before the $Ti^{3+}$ alkoxides or mixed alkoxides precipitate, or on the suspension of these alkoxides by adding a large excess of the chlorinating agent (at least one mole of chlorinating agent for each mole of alkoxide group).

When the chlorination reaction is carried out on solutions, the reaction is conducted by adding the chlorinating agent at a temperature of between 0° and 30° C.

In the case of the $Ti^{3+}$ alkoxide, the catalytic material precipitates in the form of a brown powder ($\beta$ $TiCl_3$) or violet powder ($\gamma$ or $\delta$ $TiCl_3$).

If the obtained suspensions of these catalytic materials are heated (65°–150° C.), the $\beta$ $TiCl_3$ is easily converted into the $\gamma$ form. After conversion, if necessary the catalytic material obtained is filtered, and washed with a hydrocarbon or other inert solvent, until there is no further chlorine or halogen in the filtrate, and is finally used either after drying or as a suspension in an inert material such as n-heptane or kerosene. Compared to the above mentioned patent application in which the transition metal chlorides were reduced directly by metal vapour, the system now described has the drawbacks of being able to use a more limited number of metals as the reducing agent, and to arrive possibly at the same materials but using two successive operations, the second of which consumes a considerable quantity of inorganic chlorinating agent.

In compensation, it is possible according to the new method to prepare catalytic materials in which the ratio of transition metal in its reduced state to the reducing metal can be varied at will between for example 0.5 to 10, by suitably processing the products.

It is also possible to incorporate in the catalytic materials halogens which are different from that of the metal used in the reduction, e.g. each time mixed alkoxides or solutions of two or more different alkoxides are reduced.

This is true not only for the saline chlorides such as those of Ca or Sr, but also for $AlCl_3$ or $ZrCl_4$, which could be easily introduced into a catalytic system by reducing Ti $(OR)_4$ in the presence of $Al(-O-sec.butyl)_3$ or $Zr(O-n-butyl)_4$ with Mg or Mn, followed by chlorination. Preparation of such catalytic systems would not be possible by directly reducing the chlorides, as both $ZrCl_4$ and $AlCl_3$ are insoluble in hydrocarbons. A further advantage of the new system is that the metal alkoxides are high boiling materials which do not give off hydrogen halide acids by hydrolysis or thermal decomposition, in contrast to halides.

This means that unprotected heating elements and higher reaction temperatures can be used in the reactors where vaporisation takes place, with considerable plant simplification and energy saving. Both methods allow the preparation of $TiCl_3$-based catalytic materials having a high surface area, without using metal alkyls as the reducing agent. Finally, the use of the catalytic materials prepared by product chlorination as heretofore described leads to polymers or copolymers having characteristics which are considerably better than by any other process, in particular the process described in the above mentioned patent application, these being:
  a higher yield for equal Mg/Ti ratios a narrower M.W. distribution ($MF_{21.6}/MF_{2.16}$ 25–30)
good morphology (lower content of fine powder less than 75μ), the polymers being free flowing
high apparent density (generally between 0.35 and 0.45 Kg/l).

For comparison purposes and for demonstrating the aforesaid, we have carried out examples 30, 31 of tables 5 and 33. These examples compare the results of polymerisation tests on ethylene under different conditions using one of the catalytic systems claimed in this patent application, with polymerisation tests under analogous conditions using one of the materials obtained by reducing $TiCl_4$ with Mg vapour in accordance with the above mentioned patent application.

Example 34 relates to polymerisation of propylene.

Examples 1–17 relate to the reduction of transition metal alkoxides with Mg, Al and other vapours.

EXAMPLES 1–6 furnaces or in other dead parts of the reactor. The Ti/Mg ratio varies according to reaction conditions between 2.3 (Ex. 1, almost corresponding to the pure mixed alkoxide) and 8.0 (Ex. 3, corresponding to a relatively pure Ti $(O-n-butyl)_3$). These facts are justifiable considering that because of the good evaporation efficiency, the Ti $(O-n-butyl)_4$ which has not undergone reaction competes with the Ti $(O-n-butyl)_3$ in sequestering the Mg $(O-n-butyl)_2$ to give the mixed Mg $[Ti(O-n-butyl)_6]$ alkoxide. This product is soluble in hydrocarbon, and this is the reason why soluble Mg in the mother solution is constantly found. When the reactions are carried out stoichiometrically, i.e. avoiding any excess Ti $(OR)_4$, the magnesium precipitates together with the titanium alkoxide reduced quantitatively, and neither the titanium nor the Mg can be further found by analysis in the mother solutions (Ex. 6).

All the products are largely amorphous to X-rays, and are weakly paramagnetic.

TABLE 1

Reduction of Ti(O-n-butyl)$_4$ with Mg*

| Test No. | Ti(OR)$_4$ (mM) in solution | Mg (mgA) in source | Treatment T (°C.) | Treatment t (hr) | Solution analysis after treatment Ti (mm) | Solution analysis after treatment Mg (ma) | Ti/Mg solution (mm/mm) | Mixed alkoxide analysis (insoluble) Ti (%) | Mixed alkoxide analysis (insoluble) Mg (%) | Mixed Ti/Mg alkoxide (mm/mm) | Solid product yield (g) | Evaporation efficiency Mg found Mg evaporated (%) |
|---|---|---|---|---|---|---|---|---|---|---|---|---|
| 1*** | 80 | 33 | 65 | 1 | n.d. | n.d. | — | 14.9 (13.6) | 3.25 (3.5) | 2.3 (2.0) | 6.5 | n.d. |
| 2 | 80 | 33 | 65 140 | 1 6 | 19 | 77 | 2.45 | 16.7 | 1.1 | 8.3 | 10.8 | 39 |
| 3 | 80 | 39 | 120 | 2 | 20 | 11.5 | 1.73 | 16.0 | 2.32 | 3.4 | 8.0 | 50 |
| 4 | 80 | 39 | 105 | 2 | 32 | 21 | 1.56 | 14.7 | 1.94 | 3.8 | 9.6 | 74 |
| 5 | 80 | 10.3 | 120 | 3 | n.d. | n.d. | n.d. | 16.3 | 2.1 | 3.9 | 1.5 | n.d. |
| 6** | 20 | 43 | 140 | 6 | abs. | abs. | — | 12.9 (13.2) | 7.25 (6.7) | 0.9 (1.0) | 8.1 | 56 |

*Evaporation carried out at −20° C.; vaporisation time 30 mins; solvent kerosene (pc 200–240° C.), 150 ml.
**The product is pyrophoric: Mg[Ti(OR)$_4$] has a MW of 364.2 and the analytical data in brackets.
***[Ti(OR)$_3$]$_2$ . Mg(OR)$_2$ has a MW of 704.1 and the analytical data in brackets, as would [Ti(OR)$_2$]$_2$ . Mg(OR)$_2$, Ex. 6

Reduction of $Ti^{4+}$ butoxide by Mg vapour

Table 1 shows the conditions under which Ti (O-n-butyl)$_4$ was reduced by Mg metal. The green or grey-green powdery solid products were filtered from the green-coloured kerosene after the various treatments, were washed repeatedly with n-heptane and were dried under vacuum in order to determine Ti and Mg analytically.

Analytical determinations were also carried out on the filtered solutions, which were generally of green colour.

The Mg evaporation efficiency (molar ratio of the evaporated magnesium (sum of Mg solution and solid Mg) to that located in the source) was between 50 and 70% due to metal losses on the bars supporting the

EXAMPLES 7–11

Reduction of $Ti^{4+}$ alkoxides with Mg vapour

Table 2 shows the reduction conditions for certain titanium alkoxides and the yields and characteristics of the products obtained.

The suspensions originating from the reduction reactions are of green or grey-green colour, with the exception of the Ti(O-i-propyl)$_4$, which is blue. When this particular type of suspension is heated, the Ti/Mg ratio in the precipitate changes profoundly (compare examples 9 and 10) in the opposite direction to that observed in the reduction of Ti(O-n-butyl)$_4$. This effect is due to the greater solubility of Ti(O-i-propyl)$_3$ than Ti(O-n-butyl)$_3$.

TABLE 2

Reduction of titanium alkoxides other than Ti(O-n-butyl)$_4$ with Mg*

| Test No. | Ti(OR)$_4$ (type) | (mM) | Mg (mgA) | Treatment T (°C.) | Treatment t (hr) | Solution analysis after treatment Ti (mm) | Solution analysis after treatment Mg (mm) | Ti/Mg solution (mm/mm) | Mixed alkoxide analysis Ti (%) | Mixed alkoxide analysis Mg (%) | Mixed Ti/Mg alkoxide (mm/mm) | Solid product yield (g) | Evaporation efficiency Mg found Mg evaporated (%) |
|---|---|---|---|---|---|---|---|---|---|---|---|---|---|
| 7 | Ti(OEt)$_4$ | 80 | 35 | 70 140 | 3 3 | 23 | 12 | 1.9 | 19.92 | 1.78 | 5.7 | 9.8 | 55 |
| 8 | Ti(O-n-propyl)$_4$ | 80 | 35 | 140 | 3 | 27 | 13 | 2.1 | 18.68 | 0.99 | 9.6 | 9.7 | 49 |
| 9 | Ti(O-i-propyl)$_4$ | 80 | 35 | 20 | 6 | 15 | 4 | 3.7 | 15.0 | 5.2 | 1.5 | 6.3 | 50 |
| 10 | Ti(O-i-propyl)$_4$ | 80 | 35 | 140 | 3 | 36 | 1.9 | 19 | 6.20 | 15.0 | 4.3 | 3.8 | 80 |
| 11 | Mg[T(O-n-butyl)$_4$ | | | | | | | | | | | | |

TABLE 2-continued

| | Reduction of titanium alkoxides other than Ti(O-n-butyl)$_4$ with Mg* | | | | | | | | | | | | |
|---|---|---|---|---|---|---|---|---|---|---|---|---|---|
| | | | | Treatment | | Solution analysis after treatment | | Ti/Mg solution | Mixed alkoxide analysis | | Mixed Ti/Mg alkoxide | Solid product yield | Evaporation efficiency Mg found |
| Test No. | Ti(OR)$_4$ (type) | | Mg (mgA) | T (°C.) | t (hr) | Ti (mm) | Mg (mm) | (mm/mm) | Ti (%) | Mg (%) | (mm/mm) | (g) | Mg evaporated (%) |
| | (OEt)$_2$] | 40 | 30 | 140 | 3 | 18 | 27 | 0.87 | 8.21 | 8.50 | 0.5 | 3.0 | n.d. |

*Evaporation conducted under the conditions of table 1.

EXAMPLES 12-14

Examples are given of the reduction of Ti(O-n-butyl)$_4$ with Ca or Al vapour.

The products are green, poorly soluble, and were isolated after treatments analogous to those given for the preceding examples.

EXAMPLE 17

Reduction of Ti(O-n-butyl)$_4$ with Mg in the presence of Al (O-sec.-butyl)$_3$

Mg (35 mm) is evaporated under the same conditions as examples 1-14 into a kerosene solution of Ti(O-n-butyl)$_4$ (80 mm) and Al (O-sec.-butyl)$_3$ (18 mm).

TABLE 3

| | Reduction of Ti(OR)$_4$ with vapour of metals other than Mg(M)[Ca and Al] | | | | | | | | | | | | | |
|---|---|---|---|---|---|---|---|---|---|---|---|---|---|---|
| | | | M in source | | Treatment | | Solution analysis after treatment | | Ti/M | Mixed alkoxide analysis | | Mixed Ti/M alkoxide | Mixed alkoxide product | Evaporation efficiency M evaporated |
| Test No. | Ti(OR)$_4$ type | mM | type | (mgA) | T (°C.) | t (hr) | Ti (mm) | M (mm) | (mm/mm) | Ti (%) | M (%) | (mm/mm) | yield (g) | M in source (%) |
| 12* | Ti(O—n-butyl)$_4$ | 40 | Ca | 1.5 | 140 | 3 | n.d. | n.d. | — | 15.7 (13.4) | 4.5 (5.6) | 2.5 (2.0) | 0.8 | n.d. |
| 13** | Ti(O—n-butyl)$_4$ | 20 | Al | 4.4 | 120 | 3 | n.d. | n.d. | — | 15.6 (13.7) | 4.1 (2.6) | 2.15 (3.0) | 1.5 | — |
| 14 | Ti(O—n-butyl)$_4$ | 40 | Al | 3.7 | 130 | 4 | 24.18 | 0.7 | — | 14.8 | 5.9 | 1.42 | 1.2 | 57 |

*Ca[Ti$_2$(OR)$_8$] has a MW of 720 and the analytical data in brackets
**[Ti(OR)$_4$]$_3$ . Al has a MW of 1047 and the analytical data in brackets

EXAMPLE 15

Reduction of VO(O-i-propyl)$_3$ with Mg

Under the experimental conditions of examples 1-14, Mg (47 ma) is vaporised into a kerosene solution of VO(O-i-propyl)$_3$ (100 mm). After the evaporation, the suspension is stirred for 2 hours at ambient temperature, the product is filtered off and washed with heptane and dried under vacuum (12 g, violet colour).

The product shows the following percentage analysis: V 17.9%, Mg 7.6%. [VO(O-i-propyl)$_3$] Mg comprises V 16.9%, Mg 8.0%. The V/Mg ratio is 1.1, and the vaporisation efficiency 75%.

EXAMPLE 16

Reduction of Zr(O-n-propyl)$_4$ with Mg

Under the experimental conditions of examples 1-14, Mg (40 ma) is vaporised into a kerosene solution of Zr(O-n-propyl)$_4$ (50 mm). Gas is given off during vaporisation, and care must be taken to control the reaction so that it does not become too vigorous.

It is then allowed to cool to ambient temperature while stirring vigorously, and after 4 hours the solid product is filtered off, washed repeatedly with heptane, and finally dried under vacuum (yield 1.2 g of a grey pyrophoric powdery product).

Analysis shows the following values: Zr 26.3%, Mg 1.8%.

After evaporation, it is allowed to cool to ambient temperature while stirring vigorously for 1½ hours, and is finally heated for 2 hours at 105° C.

A green powder (9.6 g) is filtered off, and is washed with heptane and dried under vacuum, to show the following composition:

Ti 14.7%; Mg 1.94%; Al 0.66%.

The filtrate contains 38 mm of Ti, 15 mm of Mg and 13 mm of Al. The vaporisation efficiency is 65%.

EXAMPLES 18-25

Reduction of alkoxides with Mg, Ca and Al vapour, and chlorination with an inorganic chlorinating agent Chlorination of mixed titanium and magnesium alkoxides with SiCl$_4$ In these examples, the non-isolated mixed alkoxides are chlorinated by means of an excess of SiCl$_4$ ($\geq$ 1 mole SiCl$_4$/mole of OR group). The chlorination is carried out by dripping pure SiCl$_4$ into the solution-suspension from the vaporisation reactor, while vigorously stirring so as to maintain the temperature around 20°-30° C. After the addition, the reaction temperature is raised to 65° C. under stirring, and is maintained for 1 hour.

Finally, the solid product is filtered off, washed with heptane until the inorganic chlorine is eliminated, and finally resuspended in n-heptane. The results of these tests and the analytical data for the products obtained are given in table 4.

All the products are of brown or red-brown colour, and are in the form of mainly weakly paramagnetic amorphous powder.

TABLE 4

Chlorination of mixed titanium alkoxides with SiCl₄

| Test No. | Ti(OR)₄ type | mM | Mg source | Treatment T (°C.) | Treatment hr | SiCl₄ (mmoles) | Chlorination treatment T (°C.) | Chlorination treatment hr | Analysis of solid material after chlorination (mm/l) Ti | Mg | Cl | Suspension volume (ml) | Mg/Ti (mmoles) in solid material | Vaporisation efficiency Mg found Mg evaporated |
|---|---|---|---|---|---|---|---|---|---|---|---|---|---|---|
| 18 | Ti(O—n-propyl)₄ | 80 | 40 | 140 | 3 | 950 | 80 | 1 | 359 | 214 | 1185 | 140 | 0.59 | 65 |
| 19 | Ti(O—n-butyl)₄ | 80 | 32 | 100 | 2 | 950 | 65 | 1½ | 211 | 130 | 840 | 150 | 0.61 | 59 |
| 20 | Mg[Ti(O—n-butyl)₄(OEt)₂] | 40 | 40 | 100 | 3 | 950 | 80 | 1 | 135.3 | 272 | 855 | 180 | 2.0 | 41 |
| 21* | Ti(O—n-butyl)₄ | — | 45 | 105 | 2 | 920 | 65 | 2 | 395 | 231 | 1495 | 80 | 0.58 | 54 |

*This preparation was carried out by vaporising the magnesium in a solution of Ti(OR)₄ and Al(O—sec-butyl)₃ (19 mm). The final product contains Al, which has a concentration of 7.45 mm/l in its suspension.

EXAMPLE 22

Chlorination of a mixed isolated Ti and Mg alkoxide with SiCl₄

40 ml of SiCl₄ in 50 cc of n-heptane were added to the product of example 2 of table 1 (2.8 g) and the mixture was stirred vigorously at ambient temperature and then for 1 hour at 65° C. The material changed from green to violet. It was filtered off, washed with heptane and finally dried under vacuum. Analysis gave the following values for the solid material obtained (1.5 g):

Ti 20.4%, Mg 2.4%, Cl 34.8%, this satisfying a crude formula of Mg₁ Ti₄.₃ Cl₁₀ (O-n-butyl)₅.₉.

EXAMPLE 23

Reduction of Ti(OR)₄ with Mn vapour, and chlorination of the resultant solution-suspension with SiCl₄

Ti(O-n-butyl)₄ (50 mm) are reduced with Mn vapour (11.8 mm) in kerosene in the manner described for examples 1–14. Without isolating the products, the suspension is directly chlorinated with SiCl₄ (430 mm), which is added at ambient temperature under stirring.

This suspension is heated to 70° C. for 1 hour, and finally the violet product is filtered off, washed with heptane and resuspended in 70 ml of n-heptane. The suspension shows the following analysis (mm/l): Ti 69.8, Mn 80.1, Cl 320.

The evaporation efficiency is 68%.

EXAMPLE 24

Reduction of Ti(O-n-butyl)₄ with Al vapour, and chlorination of the obtained mixtures with TiCl₄

Metal Al (7 mm) was vaporised into 200 ml of kerosene containing Ti(O-n-butyl)₄ (20 mm). TiCl₄ (220 mm) was added to the green suspension-solution, which was stirred for 2 hours at ambient temperature and then for 1 hour at 80° C.

The brown product obtained was then filtered off, washed repeatedly with n-heptane and resuspended in 20 ml of n-heptane, to give a suspension of the following composition (mm/l):

Ti 360, Al 138, Cl 1400

Ti/Al ratio=2.6. The vaporisation efficiency (Al analysed/Al evaporated) was 40%.

EXAMPLE 25

Reduction of Ti(O-n-propyl)₄ with Al vapour, and direct chlorination of the obtained mixtures as in example 24

Al (4.0 mm) was evaporated into a kerosene solution (150 ml) of Ti(O-n-propyl)₄ (25 mm).

The suspension-solution obtained was brought to ambient temperature, stirred at this temperature for 2 hours, after which TiCl₄ (220 mm) was added to it. It was heated to 120° C. for 1 hour while continuing stirring, the TiCl₃ was then filtered off, washed with heptane and dried under vacuum to give 1.1 g of product with the following analysis:

Ti 24.5%, Al 6.7%, Cl 66.2%

Evaporation efficiency 70%.

EXAMPLE 26

Reduction of solutions of titanium⁴⁺ and zirconium⁴⁺ alkoxide solutions in the presence of Al(O-sec-butyl)₃ with Mg vapour Mg (80 mm) was evaporated into a kerosene solution (150 ml) of Zr(O-n-butyl)₄ (n-but. OH) (40 mm), Ti(O-n-butyl)₄ (40 mm) and Al(O-sec-butyl)₃ (12 mm).

Gas is evolved during the tests, and the vaporisation is therefore carried out with some care.

The mixture was allowed to reach ambient temperature, and was then heated to 80° C. for 1 hour.

After cooling, 140 ml of SiCl₄ were dripped in, and the mixture was stirred at ambient temperature for 1 hour and finally at 60° C. for 2 hours. The brown solid was filtered off, washed repeatedly with n-heptane and resuspended in heptane (70 ml). The suspension gave the following values (mm/l) on analysis:

Ti 179.6, Zr 38.4, Al 27.80, Cl 1340, Mg 156.2.

The evaporation efficiency was 27%.

EXAMPLES 27–33

Polymerisation of ethylene with some of the products of examples 18–25 (table 5)

The polymerisations were carried out in a 2 liter autoclave temperature controlled at 85° C., by introducing successively a heptane solution of TiBAL (1 liter, 8 mm/l of TiBAL) containing the desired quantity of catalytic component (0.024–0.05 ma/l in Ti) as a hydrocarbon suspension (that of examples 19–21), then hydrogen (5 atm) and finally ethylene up to a total pressure of 15 atm. This total pressure was maintained by continuously feeding ethylene during the course of the tests (5 hours). The tests were blocked with isopropanol (5 ml), and the polyethylene obtained was dried to constant weight.

The results of the ethylene polymerisations are shown in table 5, which also gives at the end an example (31) as a test of comparison with ethylene obtained using one of the catalytic systems prepared by the procedure described in the above mentioned patent appln. and having the same Mg/Ti ratio.

The average particle size was measured by sieving the polymer powders through a series of sieves with a mesh aperture lying between 710 and 75μ.

TABLE 5

Polymerisation of ethylene with the catalytic materials described in examples 18–25 and TiBAL

| Test No. | Catalytic material used as example No. | Ti mM | Yield g | Yield Kg PE per g Ti | MF 2.16 (g/10 min) | MF 21.6/ MF 2.16 | Apparent density (Kg/l) | Shear rate sec.$^{-1}$ | Average particle size ($\mu$) 700 weight (%) | 75 weight (%) |
|---|---|---|---|---|---|---|---|---|---|---|
| 26 | 19 | 0.031 | 375 | 250 | 1.5 | 26 | 0.43 | 4 | 3.2 | 3.6 |
| 27 | 18 | 0.035 | 385 | 227 | 1.2 | 24 | 0.39 | 5 | 2.9 | 5 |
| 28 | 21 | 0.054 | 660 | 240 | 1.9 | 24 | 0.45 | 4 | 3.1 | 3.7 |
| 29 | 20 | 0.044 | 540 | 420 | 2.85 | 25 | 0.39 | 4 | 2.9 | 3.6 |
| 30* | 25 | 0.026 | 155 | 125 | 0.38 | 30 | 0.40 | 4 | 1.6 | 3.4 |
| 31** | — | 0.114 | 400 | 88 | (3.0 to 21.6 kg) | n.d. | 0.30 | does not shear | 3.1 | 32.4 |

*4 hour test;
**test with catalyst prepared as described in our patent case 940/982 Ex. 2.

EXAMPLE 33

A test was carried out with the catalytic material of Ex. 23. The polymerisation conditions were those of Ex. 26–31, except for the partial pressure of the hydrogen which in this test was 10 atm. and the polymerisation duration which was 2 hours. The titanium concentration was 0.069 mm/l.

The polythene produced was 160 g with a $MF_{2.16}$ (g/10 min) of 3.9. The production yield was 49 Kg of PE/g Ti.

EXAMPLE 34

An autoclave of 5 liters capacity temperature controlled at 85° C. was charged with 2 liters of n-heptane containing TiBAL at a concentration of 4 mm/l, and the product of Ex. 19 of table 4 at a Ti concentration of 0.063 mm/l.

The autoclave was pressurised with 2 atm. of $H_2$ and then with 3.3 atm. of $C_2H_4$, maintaining the pressure constant at 5.3 atm. for 2 hours.

The polymerisation was blocked to give 403 g of polythene with a MFI at 2.16 Kg of 1.27 (g/10 min) and $MF_{21.6}/MF_{2.16}$ of 26, with a specific activity of 10,000 g PE/g Ti$\times$hr.$\times$atm.

The polymer was free flowing with an apparent density of 0.367 Kg/l.

A polymerisation test under identical conditions to those stated heretofore with the material prepared in Ex. 2 of our patent case 940–982 gave 278 g of polythene, with a MFI of 0.06 (g/10 min), $MF_{21.6}/MF_{2.16}$ of 45 and a specific activity of 7000 PE g/g Ti$\times$hr.$\times$atm.

The polymer was not free flowing, and had an apparent density of 0.21 Kg/l.

EXAMPLE 35

Polymerisation of propylene

The catalytic material prepared in Ex. 19 of table 4 was used in polymerising propylene under the following conditions: 0.5 l of n-heptane containing component 19 (TI) 2 mm/l, Al Et$_2$ Cl 8 mm/l, Al Et$_3$ 0.8 mm/l was fed into a 1 liter autoclave temperature controlled at 70° C., and pressurised with 7 atm. of propylene immediately after introducing the catalytic components. The pressure was maintained constant for 90 minutes. After venting the autocalve, 75 g of polypropylene were recovered.

We claim:

1. A process for reducing alkoxides of transition metals selected from the group consisting of Ti (4+), V (4+), V (5+), Cr (4+), and Zr (4+), to the corresponding alkoxides of lower valency, consisting essentially of reacting at least one member of said alkoxides of said metals in the liquid phase with the vapours of at least one metal selected from the group consisting of alkaline earth, group III and group IV metals, and manganese.

2. A process as claimed in claim 1, wherein the alkoxide and metal are reacted in a molar ratio of about between 1:1 and 50:1.

3. A process as claimed in claim 2, wherein the reaction is carried out at a temperature of about between −80° and +20° C.

4. A process as claimed in claim 2, wherein the reaction is carried out at a pressure of about between $1.0^{-5}$ mm and atmospheric pressure.

* * * * *